US012227790B2

United States Patent
Yan et al.

(10) Patent No.: US 12,227,790 B2
(45) Date of Patent: Feb. 18, 2025

(54) SOLID PHASE EXTRACTION MATERIAL AND ITS USE FOR NUCLEIC ACID ENRICHMENT AND DETECTION

(71) Applicants: CAPITALBIO CORPORATION, Beijing (CN); TSINGHUA UNIVERSITY, Beijing (CN)

(72) Inventors: He Yan, Beijing (CN); Wanli Xing, Beijing (CN); Ying Lu, Beijing (CN)

(73) Assignees: CAPITALBIO CORPORATION, Beijing (CN); TSINGHUA UNIVERSITY, Beijing (CN)

( * ) Notice: Subject to any disclaimer, the term of this patent is extended or adjusted under 35 U.S.C. 154(b) by 133 days.

(21) Appl. No.: 17/822,521

(22) Filed: Aug. 26, 2022

(65) Prior Publication Data

US 2022/0396827 A1 Dec. 15, 2022

Related U.S. Application Data (62) Division of application No. 16/630,821, filed as application No. PCT/CN2018/095600 on Jul. 13, 2018, now abandoned.

(30) Foreign Application Priority Data

Jul. 14, 2017 (CN) .......................... 201710575341.5

(51) Int. Cl.
*C12N 15/00* (2006.01)
*C12N 15/10* (2006.01)
(Continued)

(52) U.S. Cl.
CPC ....... *C12Q 1/6806* (2013.01); *C12N 15/1006* (2013.01); *C12N 15/1013* (2013.01); *C12Q 1/6844* (2013.01)

(58) Field of Classification Search
None
See application file for complete search history.

(56) References Cited

U.S. PATENT DOCUMENTS

2013/0029333 A1 1/2013 Son et al.
2016/0289733 A1* 10/2016 Li ........................ C12Q 1/6823

FOREIGN PATENT DOCUMENTS

CN 103411933 A 11/2013
CN 104569101 A 4/2015
(Continued)

OTHER PUBLICATIONS

Pham et al., Graphene Oxide Conjugated Magnetic Beads for RNA Extraction, Chem Asian J. Aug. 4, 2017;12(15):1883-1888. doi: 10.1002/asia.201700554. Epub Jun. 22, 2017.*
(Continued)

*Primary Examiner* — Aaron A Priest
(74) *Attorney, Agent, or Firm* — Knobbe, Martens, Olson & Bear, LLP

(57) ABSTRACT

A method of enriching nucleic acid, including mixing a sample with a solid phase extraction material; and separating the solid phase extraction material; wherein the solid phase extraction material is glass beads or magnetic beads modified with reduced graphene oxide. Also disclosed is a method of detecting nucleic acid, including mixing a nucleic acid sample enriched by the method above with a probe; and amplifying and detecting an amplification product by electrophoresis.

7 Claims, 3 Drawing Sheets

Specification includes a Sequence Listing.

(51) Int. Cl.
  *C12Q 1/6806* (2018.01)
  *C12Q 1/6844* (2018.01)

(56) References Cited

FOREIGN PATENT DOCUMENTS

| CN | 105300950 A | 2/2016 |
|---|---|---|
| CN | 105713900 A | 6/2016 |
| CN | 105754991 A | 7/2016 |
| CN | 106596696 A | 4/2017 |
| CN | 106710762 A | 5/2017 |
| CN | 107236730 A | 10/2017 |
| CN | 1077236730 A | 10/2017 |
| EP | 1 260 595 A2 | 11/2002 |
| KR | 101442418 B1 | 9/2014 |
| KR | 10-1721796 B1 | 3/2017 |
| WO | WO 2016/084945 A1 | 6/2016 |
| WO | WO 2019/011322 A1 | 1/2019 |

OTHER PUBLICATIONS

Lu et al., Comparison of Graphene Oxide and Reduced Graphene Oxide for DNA Adsorption and Sensing, Langmuir 2016, 32, 41, 10776-10783, Publication Date:Sep. 26, 2016.*

Second Office Action in Japanese Counterpart Patent Application No. 2020-501537 issued Nov. 1, 2022.

Wang et al., Partially reduced graphene oxide as highly efficient DNA nanoprobe, *Biosensors and Bioelectronic*, Jun. 15, 2016;80:140-145 (Accepted copy submitted in 17 pages).

Akceoglu, Garbis Atam, "Synthesis and Surface Modification of Graphite Oxide-Cellulose Composites for Solid Phase DNA Extraction Applications," A Doctoral Dissertation Dec. 2015.

Chandra et al., Water-Dispersible Magnetite-Reduced Graphene Oxide Composites for Arsenic Removal, ACS Nano 2010, 4, 7, 3979-3986, Publication Date: Jun. 16, 2010.

First Chinese Office Action in priority CN Patent Application No. 201710575341.5 issued Feb. 26, 2020.

Second Chinese Office Action, in Chinese Patent Application No. 201710575341.5, issued Sep. 2, 2020.

Third Chinese Office Action in CN 201710575341.5 issued Feb. 22, 2021.

European Office Action in European Patent Application No. 18832.077.4 issued Oct. 15, 2021.

Extended European Search Report in EP18832077.4 issued Feb. 22, 2021.

Hashemi, et al., "DNA and RNA extractions from eukaryotic and prokaryotic cells by graphene nanoplatelets", RSC Adv., 2014, 4, 60720-60728.

He, Hui, et al., "Integrated DNA and RNA extraction using magnetic beads from viral pathogens causing acute respiratory infections," Scientific Reports, vol. 7, p. 45199, Mar. 23, 2017.

Huang et al., Ionic liquid-coated Fe3O4/APTES/graphene oxide nanocomposites: synthesis, characterization and evaluation in protein extraction processes, RSC Adv., 2016, 6, 5718-5728, Dec. 23, 2015.

International Search Report and Written Opinion, mailed Sep. 30, 2018 in PCT/CN2018/095600.

Japanese Office Action in Japanese Patent Application No. 2020-501537, issued Apr. 5, 2022.

Kumar, Sunny, et al., "Graphene based multifunctional superbots," Carbon 89 (2015) 31-40.

Lu, Chang, et al., "Comparing Graphene Oxide and Reduced Graphene Oxide for DNA Adsorption and Sensing," Langmuir, Sep. 26, 2016.

Pham, Xuan-Hung, et al., "Graphene Oxide Conjugated Magnetic Beads for RNA Extraction," Chem. Asian J. Jun. 22, 2017, No. 12, vol. 15, pp. 1883-1888.

Sun et al., Magnetite/Reduced Graphene Oxide Nanocomposites: One Step Solvothermal Synthesis and Use as a Novel Platform for Removal of Dye Pollutants, Nano Res. 2011, 4(6): 550-562.

Van Nguyen, et al., "Effect of glass surface treatments on the deposition of highly transparent reduced graphene oxide films by dropcasting method", Colloids and Surfaces A: Physiochem. Eng. Aspects 498 (2016) 231-238.

Yan et al., "Reduced Graphene Oxide-Based Solid-Phase Extraction for the Enrichment and Detection of microRNA", Analytical Chemistry, 2017, 89, 19, 10137-10140, Publication Date: Sep. 21, 2017.

Yang et al., Graphene-coated materials using silica particles as a framework for highly efficient removal of aromatic pollutants in water, Scientific Reports vol. 5, Article No. 11641 (2015).

Ye, Guofeng and Beverly, Michael, "The use of strong anion-exchange (SAX) magnetic particles for the extraction of therapeutic siRNA and their analysis by liquid chromatography/mass spectrometry," Rapid Communications in Mass Spectrometry, vol. 25, No. 21 Oct. 3, 2011, pp. 3207-3215.

Zhou, Ming, et al., "Electrochemical Sensing and Biosensing Platform Based on Chemically Reduced Graphene Oxide", Anal. Chem. 2009, 81, 5603-5613.

Zhu, Shenmin, et al., "Sonochemical fabrication of $Fe_3O_4$ nanoparticles on reduced graphene oxide for biosensors", Ultrasonics Sonochemistry, vol. 20, Issue 3, May 2013, pp. 872-880.

Zhu, Xiaoli, et al., "Detection of microRNA SNPs with ultrahigh specificity by using reduced graphene oxide-assisted rolling circle amplification," Electronic Supplementary Material (ESI) for ChemComm, Dec. 31, 2015, No. 51, pp. 10002-10005.

* cited by examiner

SOLID PHASE EXTRACTION MATERIAL AND ITS USE FOR NUCLEIC ACID ENRICHMENT AND DETECTION

CROSS REFERENCE TO RELATED APPLICATIONS

This application is a divisional application of U.S. application Ser. No. 16/630,821, which is a U.S. National Phase of International Application No.: PCT/CN2018/095600, filed Jul. 13, 2018 designating the U.S., and published as WO 2019/011322 A1 on Jan. 17, 2019, which claims the priority of Chinese Patent Application No. 201710575341.5, filed on Jul. 14, 2017 and titled with "SOLID PHASE EXTRACTION MATERIAL AND ITS USE FOR NUCLEIC ACID ENRICHMENT AND DETECTION", the disclosure of which is incorporated herein by reference.

REFERENCE TO SEQUENCE LISTING

A Sequence Listing submitted as an XML file via Patent Center is hereby incorporated by reference in accordance with 35 U.S.C. § 1.52(e). The name of the XML file for the Sequence Listing is UTLN024.001D1.xml, the date of creation of the XML file is Aug. 26, 2022, and the size of the XML file is 4.77 KB.

FIELD

The present invention relates to the technical field of analytical chemistry and biological detection, in particular to a solid phase extraction material and its use for nucleic acid enrichment and detection.

BACKGROUND

MicroRNAs (miRNAs) are non-encoding, single-stranded RNA molecules of about 22 nucleotides in length that are encoded by endogenous genes and are mainly involved in the regulation of post-transcriptional gene expression. They can bind to the target mRNA to silence or reduce the expression of the target gene, so as to play a role in regulating the body. Because the change of miRNA content is often closely related to the occurrence of cancer, the detection of miRNA is an important step of many nucleic acid detection techniques. The commonly used miRNA detection methods are poly (A) tailed RT-PCR and stem-loop primer RT-PCR. The former cannot distinguish pri-miRNAs or pre-miRNAs during sample preparation, so accurate quantification of miRNAs cannot be achieved. The latter usually does not anneal to the pre-miRNA, but the primer design is difficult and the condition of the stem loop formation is stricter. In recent years, scientists have developed a variety of new techniques for miRNA detection, in which rolling circle amplification (RCA) is widely used in the detection of miRNAs. miRNAs are short single-stranded RNAs that match the detection targets of RCA (short single-stranded nucleic acids). In the presence of a circular probe, the miRNA is complementarily paired with a portion thereof, and subjected to isothermal amplification under the action of a Bst enzyme or a phi29 enzyme. However, conventional RCAs cannot distinguish between homologous miRNAs, i.e., miRNAs that differ by only one or two bases.

Graphene is a two-dimensional crystal consisting of monoatomic layer carbon atoms with a honeycomb-like hexagonal lattice structure via sp2 hybrid orbitals. According to relevant literature, graphene oxide (GO) or reduced graphene oxide (rGO) is rich in π-electron clouds and oxygen-containing groups, they can adsorb short single-stranded nucleic acid quickly via π-π interaction, hydrogen bond and electrostatic interaction. Their adsorption capacity and adsorption rate for long-chain nucleic acid and double-stranded nucleic acid are weak. In addition, rGO or GO can quench the fluorescent groups near it. Solid phase extraction technique is a sample pretreatment technique in analytical chemistry, which can enrich samples and greatly increase the sensitivity of detection. However, present studies show that high concentrations of rGO or GO in the reaction system inhibit the RCA reaction. There is no literature or patent report that graphene is capable of adsorbing short single-stranded nucleic acids and graphene can be used in solid phase extraction technique for miRNA enrichment and amplification.

SUMMARY

In view of this, the technical problem to be solved by the present invention is to provide a solid phase extraction material and its use for nucleic acid enrichment and detection. The solid phase extraction material provided by the present invention has a surface loaded with graphene oxide (GO) or reduced graphene oxide (rGO) for the extraction and enrichment of miRNA, decreasing detection limit of miRNA by RCA, which is conducive to the detection of trace miRNA. And due to the use of rGO, the ability of RCA to distinguish between homologous miRNAs is greatly enhanced.

The solid phase extraction material provided by the present invention, wherein the solid phase support of the solid phase extraction material is modified at its surface with graphene oxide or reduced graphene oxide.

In the present invention, the solid phase support is glass beads or magnetic beads. The diameter of the glass beads affects the specific surface area, thereby affecting the efficiency of adsorption. In the present invention, the diameter of the glass beads is 100 μm to 300 μm. In some specific embodiments, the glass beads have a diameter of 200 μm. The magnetic beads have a diameter of 10 nm to 5 μm.

In an embodiment of the present invention, the solid phase extraction material is: glass beads modified with graphene oxide at its surfaces, glass beads modified with reduced graphene oxide at its surfaces, magnetic beads modified with graphene oxide at its surfaces, or magnetic beads modified with reduced graphene oxide at its surfaces.

The solid phase extraction material provided by the present invention is made of a positively charged solid phase support adsorbed with graphene oxide or reduced graphene oxide. GO or rGO forms a thin film on the glass bead surface, or GO or rGO binds to the surface of spherical magnetic bead, so that the obtained solid phase extraction material can adsorb nucleic acid. When magnetic beads are used as the solid phase support, the magnetic beads bind to negative groups on the surface of the graphene, so that one or more magnetic beads can bind to the flat surface of graphene.

GO and rGO modified solid phase extraction materials adsorb nucleic acids through electrostatic force and hydrogen bond, π-π force, and the materials show a faster adsorption rate and higher capacity for short single-stranded nucleic acids (such as ssDNA or miRNA) than for double-stranded nucleic acids and long single-stranded nucleic acids. Compared to GO, rGO has a stronger ability to adsorb short single-stranded nucleic acids. The method for preparing the solid phase extraction material provided by the present invention comprises mixing and adsorbing a dispersion of graphene oxide or reduced graphene oxide with a solid phase support to obtain the solid phase extraction material, wherein the solid phase support is glass beads or magnetic beads.

In order to be able to adsorb graphene, the surface of the solid phase support has positively charged groups, which can bind to the negatively charged groups on the graphene surface by electrostatic interaction.

In the embodiments of the present invention, the glass beads for preparing the solid phase extraction material are glass beads with positive charges on the surface. In some embodiments, the modified silanized glass beads are used. The silanized glass beads can be commercially available or homemade, which is not limited in the present invention. The silanized glass beads were prepared by activating the surface of the glass beads with concentrated sulfuric acid and hydrogen peroxide and silanizing with APTES in ethanol solvent. The silanized glass beads have amino groups on their surface and thus have positive charges. In order to ensure a suitable specific surface area for effective adsorption of nucleic acids, the glass beads have a diameter of 200 μm.

In the present invention, the magnetic beads for preparing the solid phase extraction material are magnetic beads with positive charges on the surface; in some embodiments, amino magnetic beads are used.

In the embodiment of the present invention, the solvent in the dispersion of graphene oxide or reduced graphene oxide is water. That is, an aqueous dispersion of GO or rGO is used, which may be purchased or self-made, and there is no limit in the present invention. In the embodiments of the present invention, the lateral size of GO is 0.5-2 μm and the concentration is 1 mg/mL. The lateral size of rGO is 0.5-2 μm and the concentration is 1 mg/mL.

In the method of the present invention, the adsorption condition is shaking at room temperature for 0.5 h to 2 h. In a specific embodiment, the adsorption condition is shaking at room temperature for 1 h.

Specifically, GO modified glass beads are prepared by mixing silanized glass beads with a GO dispersion, shaking at room temperature for 1 h, washing with water and drying to obtain GO modified glass beads. In the GO dispersion, the lateral size of the GO is 0.5-2 μm and the concentration is 1 mg/mL. The drying temperature is 80° C.

Specifically, rGO modified glass beads are prepared by mixing silanized glass beads with an rGO dispersion, shaking at room temperature for 1 h, washing with water and drying to obtain rGO modified glass beads. In the dispersion of rGO, the lateral size of the rGO is 0.5-2 μm and the concentration is 1 mg/mL. The drying temperature is 80° C.

Silanized glass beads are either commercially available or homemade.

Method for preparing the silanized glass beads used in the present invention is:

mixing glass beads with concentrated sulfuric acid, slowly adding hydrogen peroxide to the mixture, shaking for 1 h, washing with pure water 10 times, drying; and mixing the glass beads with a silanization reagent, vortexing for 2 hours, and washing with pure water 10 times to obtain silanized glass beads.

The volume ratio of hydrogen peroxide to concentrated sulfuric acid is 3:7. Each 0.5 g of acid-washed glass beads is mixed with 7 mL of concentrated sulfuric acid. The concentration of sulfuric acid in the concentrated sulfuric acid is 98%.

The silanizaition reagent is APTES; the solvent is a mixture of ethanol, water, and glacial acetic acid; wherein the volume ratio of ethanol, water, and glacial acetic acid is 900:100:1; the volume ratio of the silanization reagent to the solvent is 1:50.

Specifically, GO modified magnetic beads are prepared by mixing amino magnetic beads with a GO dispersion, shaking at room temperature for 1 h, washing with water and drying to obtain GO modified magnetic beads. In the GO dispersion, the lateral size of the GO is 0.5-2 μm and the concentration is 1 mg/mL. The drying temperature is 80° C.

Specifically, rGO modified magnetic beads are prepared by mixing amino magnetic beads with a rGO dispersion, shaking at room temperature for 1 h, washing with water and drying to obtain rGO modified magnetic beads. In the dispersion of rGO, the lateral size of the rGO is 0.5-2 82 m and the concentration is 1 mg/mL. The drying temperature is 80° C.

The amino magnetic beads are APTES-modified magnetic beads with a particle size of 500 nm. In the present invention, an amino magnetic beads suspension with a concentration of 10 mg/mL is purchased from Beaver Company. Prior to the modification of GO or rGO, the magnetic beads are washed 3 times with pure water and then centrifuged to collect the magnetic beads by removing water. The magnetic beads collected from 100 μL amino magnetic beads suspension is added to 300 μL of GO or rGO dispersion.

Magnetic beads or glass beads without modification by GO or rGO have no capability of adsorbing nucleic acid. The solid phase extraction materials prepared by the method provided by the present invention are modified with GO or rGO is black, having the ability to adsorb nucleic acid.

The present invention also provided use of the solid phase extraction material for enrichment and/or detection of nucleic acid.

In some embodiments, the solid phase extraction material provided by the present invention is use for extraction and/or detection of short single-stranded nucleic acid. In some specific embodiments, the short single-stranded nucleic acid is miRNA or ssDNA.

The experiments of the present invention show that GO modified glass beads can enrich miRNA or ssDNA; and target nucleic acid molecule can be identified through specific probe, so as to realize qualitative or quantitative detection of target nucleic acid molecule. In addition, the enrichment by GO modified glass beads is mainly through electrostatic interaction, hydrogen bond, and π-π C interaction, therefore suitable for a variety of nucleic acids. The GO modified glass beads not only can adsorb miRNAs or ssDNA rapidly, but also can adsorb gDNA or mRNA (longer time is needed for the adsorption of long-chain nucleic acid or double-stranded nucleic acid). Therefore, when the adsorption time is short, the GO modified solid phase extraction material can distinguish short single-stranded nucleic acid from double-stranded nucleic acid or long-stranded nucleic acid. In the embodiments of the present invention, the adsorption time of the GO modified solid phase extraction material for short single-stranded nucleic acid is 10 minutes. The rGO modified magnetic beads adsorb the nucleic acid mainly through π-π force, which have stronger adsorption ability for nucleic acid with excess π-bond, especially short single-stranded nucleic acid such as miRNA or ssDNA. While for mRNA with a long molecular chain, the adsorption efficiency of the rGO modified magnetic beads is less, thus it can be easily distinguished from short single-stranded nucleic acid.

The GO modified solid phase extraction material provided by the present invention is used for the enrichment and/or detection of nucleic acid.

The rGO modified solid phase extraction material provided by the present invention is used for the enrichment and/or detection of short single-stranded nucleic acid.

The present invention also provides a kit for nucleic acid enrichment, comprising the solid phase extraction material of the present invention.

The kit for short single-stranded nucleic acid enrichment comprises the rGO modified or GO modified solid phase extraction material. According to the requirements of the experiment, the kit also comprises EP tube, washing buffer, and elution buffer.

The kit for the enrichment of various nucleic acids comprises a GO modified solid phase extraction material. According to the requirements of the experiment, the kit also comprises EP tubes, washing buffer, and elution buffer. The various nucleic acids comprise short single-stranded and double-stranded nucleic acids.

The present invention provides a method for enriching nucleic acid: mixing a sample with the solid phase extraction material of the present invention, separating the solid phase extraction material after extraction, washing and eluting to obtain a nucleic acid solution.

The present invention provides a method for enriching short single-stranded nucleic acid comprising: mixing a sample with the rGO modified solid phase extraction material, separating the solid phase extraction material after extraction, washing and eluting to obtain a nucleic acid solution. The extraction time is 10 min and the extraction temperature is room temperature, specifically 18-30° C.

Alternatively, based on the property that the adsorption of short single-stranded nucleic acids by GO in the GO modified solid phase extraction material is faster, the extraction time can be controlled to 10 min to achieve the specific enrichment for short single-stranded nucleic acid by using GO modified solid phase extraction material.

A method for enriching short single-stranded nucleic acid is performed by mixing a sample with the GO modified solid phase extraction material, separating the solid phase extraction material after extraction at room temperature for 10 minutes, washing and eluting to obtain a nucleic acid solution.

A method for enriching multiple nucleic acids is performed by mixing a sample with the GO-modified solid phase extraction material, separating the solid phase extraction material after extraction, washing and eluting to obtain a nucleic acid solution. In order to achieve the simultaneous enrichment of different types of nucleic acids, the extraction time in this method is not less than 1 h.

In the method provided by the present invention, when the solid phase support is glass bead, a rotator is used for the mixing during the extraction. When the solid phase support is magnetic bead, vortex is performed once every 2 min.

Since impurities such as proteins may affect the extraction performance of the solid phase extraction material according to the present invention, the sample described herein is a nucleic acid solution, for example, a low concentration extraction solution obtained after removing impurities such as proteins during a nucleic acid extraction process. Magnetic beads or membrane filtration method is used to enrich a low concentration nucleic acid extraction solution in the prior art. These methods have difficulty to enrich trace nucleic acid molecule. They are mainly suitable for extracting nucleic acid over 200 nt; for miRNA, the adsorption effect is even worse. So the amount of miRNA in RNA extracted by magnetic beads or membrane filtration method is very low. Even if a special filter membrane suitable for miRNA is used, a large amount of irrelevant RNAs exist in the obtained product, which affects the accuracy and sensitivity of subsequent detection. The solid phase extraction material prepared in the present invention has a good enrichment result even for trace nucleic acid molecule, thereby reducing the detection threshold of RCA by 25 times. In the embodiments of the present invention, a standard nucleic acid solution is used as a sample for the convenience and rigorousness of the experiments.

The standard solution is prepared from nucleic acid and buffer containing 20 mM Tris-HCl, 5 mM magnesium chloride and 50 mM sodium chloride, pH 8.0.

The present invention also provides a kit for nucleic acid detection, comprising the solid phase extraction material of the present invention, specific probe and in situ amplification reagent.

The detection kit for short single-stranded nucleic acid provided by the present invention comprises rGO modified solid phase extraction material, specific probe and in situ amplification reagent; alternatively, GO modified solid phase extraction material, specific probe and in situ amplification reagent. The specific probe is designed for detecting the target nucleic acid.

The in situ amplification reagent comprises an RCA amplification enzyme and an RCA mastermix is used in the present invention.

According to the requirements of the experiment, the kit also comprises EP tubes or a 96-well plate.

The detection kit for various nucleic acids comprises GO modified solid phase extraction material, specific probe and in situ amplification reagent. The specific probe is designed for detecting the target nucleic acid.

The in situ amplification reagent comprises an RCA amplification enzyme and an RCA mastermix is used in the present invention.

According to the requirements of the experiment, the kit also comprises EP tubes or a 96-well plate.

The present invention also provides a method of nucleic acid detection, comprising mixing a sample with the solid phase extraction material of the present invention, separating the solid phase extraction material after extraction, mixing with the specific probe and the in situ amplification reagent and amplifying, and detecting the amplification product by electrophoresis.

The solid phase extraction material is modified with rGO or GO for the detection of short single-stranded nucleic acids. It is also possible to use GO modified solid phase extraction material to detect double-stranded nucleic acids by extending the extraction time and then performing in situ amplification.

After amplification, according to the appearance of the electrophoresis band, the target nucleic acid molecule in the sample targeted by the specific probe exists is determined.

In an embodiment of the present invention, a method for enriching ssDNA is provided, which comprises: mixing a sample solution with GO modified glass beads, extracting for 10 minutes, discarding the solution, washing the glass beads and eluting to obtain an ssDNA solution.

In an embodiment of the present invention, a method for detecting ssDNA (22 nt) is also provided, which comprises: mixing a sample solution with GO modified glass beads, extracting for 10 min, discarding the solution, mixing the glass beads, RCA mastermix, circular probe and water, subjecting the mixture to isothermal amplification at 65° C. for 1.5 h, and then detecting the amplification product by electrophoresis.

In an embodiment of the present invention, a method for enriching miRNA is provided, which comprises: mixing a sample solution with rGO modified magnetic beads, extracting for 10 minutes, discarding the solution, washing the magnetic beads and eluting to obtain a miRNA solution.

The rGO modified solid phase extraction material provided by the present invention can specifically adsorb miRNA or ssDNA but not gDNA or mRNA.

In an embodiment of the present invention, a method for detecting miRNA is also provided, which comprises: mixing a sample solution with rGO modified magnetic beads, extracting for 10 minutes, discarding the solution, mixing magnetic beads, RCA mastermix, ring probe and water, subjecting the mixture to isothermal amplification at 65° C. for 1.5 h, and then detecting the amplification product by electrophoresis.

The rGO modified solid phase extraction material provided by the present invention can effectively adsorb miRNA and retain the ability to distinguish homologous miRNAs.

The present invention provides an rGO or GO modified solid phase extraction material. The GO or rGO modified solid phase extraction material can adsorb nucleic acid, especially short single-stranded nucleic acid through electrostatic force and hydrogen bond and π-π force. The solid phase extraction material provided by the present invention can enrich the nucleic acid, thereby reducing the detection limit of the sample and improving the detection sensitivity.

DETAILED DESCRIPTION

The present invention provides a solid phase extraction material and its use for the enrichment and detection of short single-stranded nucleic acid. Those skilled in the field can learn from the content herein and appropriately improve the process parameters. In particular, it should be noted that all similar replacements and modifications will be apparent to those skilled in the art, and they are all deemed to be included in the present invention. The method and application of the present invention have been described through the preferred embodiments, and it is apparent to those skilled in the art that the methods and applications herein may be modified or appropriately changed and combined without departing from the spirit, scope, and scope of the present invention to implement and use the present invention.

The magnetic beads of the present invention are biological magnetic beads and are superparamagnetic beads with a fine particle size.

The glass beads of the present invention are experimental glass beads, which are also called glass microbeads.

The short single-stranded nucleic acid according to the present invention refers to short, single-stranded nucleic acid molecule such as miRNA and ssDNA.

The various nucleic acids described in the present invention refer to various types of nucleic acid molecules such as gDNA, cDNA, cpDNA, msDNA, mtDNA, rDNA, ssDNA, miRNA, mRNA, tRNA, rRNA, tmRNA, snRNA, snoRNA, piRNA, or aRNA.

The enrichment according to the present invention refers to a step of collecting a nucleic acid of interest from a sample, and can also refer to extraction or purification.

The detection according to the present invention refers to a process of quantitative or qualitative analysis of the target nucleic acid in a sample based on the amplification result by a specific probe.

Unless otherwise specified, the room temperature of the present invention is 18-30° C.

The instruments and materials used in the present invention are all common commercial products and are all available in the market.

The following further describes the present invention in combination with examples:

EXAMPLES

Example 1

About 0.5 g of acid-washed glass beads (Sigma) was added to a beaker, 7 mL of concentrated sulfuric acid was added to the beaker, and then 3 mL of hydrogen peroxide was slowly added. The reaction system was shaken on a shaker for 1 h to complete the activation of the glass beads. After activation, the glass beads were washed 10 times with pure water and placed in an oven to dry.

The dried glass beads were put into a 1.5 mL centrifuge tube, and silanization reagent and solvent (1 mL solvent, the ratio of ethanol to water 9:1, 1 μL glacial acetic acid; 20 μL APTES as silanization reagent) were added. The reaction was carried out for 2 h with shaking and the glass beads were washed with pure water 10 times.

The excess water was removed from the glass beads and 200 μL of water and 50 μL of GO dispersion (purchased from Xianfeng Nano, with a lateral size of 0.5-2 μm and an initial concentration of 1 mg/mL) were added to the silanized glass beads. The reaction was carried out for 1 h with shaking. The glass beads then were washed by water and dried at 80° C.

Example 2

About 0.5 g of acid-washed glass beads (Sigma) was added to a beaker, 7 mL of concentrated sulfuric acid was added to the beaker, and then 3 mL of hydrogen peroxide was slowly added. The reaction system was shaken on a shaker for 1 h to complete the activation of the glass beads. After activation, the glass beads were washed 10 times with pure water and placed in an oven to dry.

The dried glass beads were put into a 1.5 mL centrifuge tube, and silanization reagent and solvent (1 mL solvent, the ratio of ethanol to water 9:1, 1 μL glacial acetic acid; 20 μL APTES as silanization reagent) were added. The reaction was carried out for 2 h with shaking and the glass beads were washed with pure water 10 times.

The excess water was removed from the glass beads and 200 μL of water and 50 μL of rGO dispersion (purchased from Xianfeng Nano, with a lateral size of 0.5-2 μm and an initial concentration of 1 mg/mL) were added to the silanized glass beads. The reaction was carried out for 1 h with shaking. The glass beads then were washed by water and dried at 80° C.

Example 3

APTES-modified magnetic beads were purchased from Beaver Company (particle size 500 nm, original concentration 10 mg/mL). 100 μL magnetic beads were put into a 1.5 mL centrifuge tube and placed on a magnetic stand to collect the magnetic beads, and excess water was removed. The magnetic beads were washed 3 times with pure water, and excess water was removed. 300 μL of GO dispersion (purchased from Xanfeng Nano, with a lateral size of 0.5-2 μm, an initial concentration of 1 mg/mL) was added to the magnetic beads. The reaction was carried out for 1 h with shaking to ensure the fully binding of the magnetic beads with GO. Excess unbound GO was removed and the magnetic beads were washed with water until the supernatant became clear. The obtained GO modified magnetic beads were dispersed in 200 μL of water and stored at 4° C.

Example 4

APTES-modified magnetic beads were purchased from Beaver Company (particle size 500 nm, original concentration 10 mg/mL). 100 μL magnetic beads were put into a 1.5 mL centrifuge tube and placed on a magnetic stand to collect the magnetic beads, and excess water was removed. The magnetic beads were washed 3 times with pure water, and excess water was removed. 300 μL of rGO dispersion (purchased from Xanfeng Nano, with a lateral size of 0.5-2 μm, an initial concentration of 1 mg/mL.) was added to the magnetic beads. The reaction was carried out for 1 h with shaking to ensure the fully binding of the magnetic beads with rGO. Excess unbound rGO was removed and the magnetic beads were washed with water until the supernatant became clear. The obtained rGO modified magnetic beads were dispersed in 200 μL of water and stored at 4° C.

Test: Verification of Effectiveness

1. Enrichment of Short Single-Stranded DNA (22 nt) by GO Modified Glass Beads

First, 25 μL of sample solution was prepared, containing ssDNA (sequence: 5'-TGAGGTAGTAGGTTGTATAGTT-3') with a final concentration of 10 nM. 0.005 g of the GO modified glass beads prepared in Example 1 (extraction material) was weighed in a 0.2 mL centrifuge tube. After 20 μL of the sample solution was added to the centrifuge tube containing the extraction material, the extraction material and the solution were mixed well by vortex. Extraction was carried out at room temperature for 10 min. After the extraction, the liquid in the centrifuge tube was aspirated and the obtained extraction material was subjected to subsequent RCA.

The non-enriched (original) sample solution was amplified as a control. The volume of the RCA reaction was 20 μL, containing 10 μL of RCA mastermix, 2 μL of sample solution, 2 μL of circular probe (sequence: CACGC-GATCCGCAACTATACAACCTACTACCT-CAACACCCTCCAACCACCAAGGC AATGTA-CACGAATTCGCCGAACG), and 6 μL of water. The reaction system was mixed well and then incubated at 65° C. for isothermal amplification. The reaction duration was 1.5 h, which was called original solution amplification.

For solid phase extraction material, 10 μL of RCA master mix, 2 μL of circular probe and 8 μL of water were added to the centrifuge tube containing the material. The reaction system was mixed well and then incubated at 65° C. for isothermal amplification. The reaction duration was 1.5 h, which was called in situ amplification.

Figure 1:
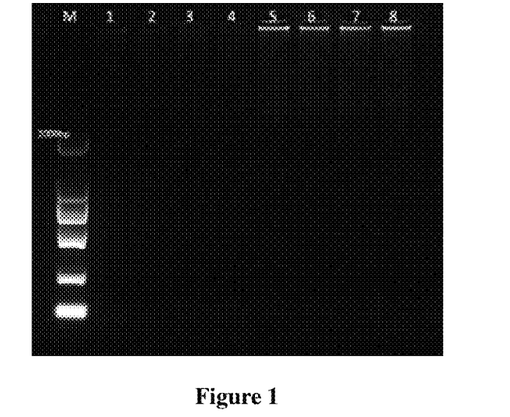
FIG. 1 shows the enrichment of ssDNA by GO modified glass beads; M is a DNA marker, lanes 1-4 are original solution amplifications; lanes 4-8 are in situ amplifications.

The products of original solution amplification and in situ amplification were subjected to electrophoresis, respectively. The results were shown in FIG. 1: M was a DNA marker, lanes 1-4 were four replicates of the original solution amplification, and lanes 5-8 were four replicates of the in situ amplification. As shown in FIG. 1, in the sample solution before the enrichment, the concentration of ssDNA was not sufficient to be amplified to generate enough RCA products to show a bright band in gel electrophoresis. However, after the enrichment by GO modified glass beads, the amount of RCA products was significantly increased, and bright bands can be seen in the electrophoresis picture. This experiment demonstrates that GO modified glass beads are capable of efficiently enriching short single-stranded DNA and undergoing in situ amplification.

2. Enrichment of miRNA let-7a (22nt) by rGO Modified Magnetic Beads

First, 25 μL of sample solution was prepared, containing let-7a (sequence: 5'-UGAGGUAGUAGGUUGUAUAGUU-3') with a final concentration of 10 nM. 0.5 μL of the rGO modified magnetic beads prepared in Example 3 (extraction material) was weighed in a 0.2 mL centrifuge tube. After 20 μL of the sample solution was added to the centrifuge tube containing the extraction material, the extraction material and the solution were mixed well by vortex. Extraction was carried out at room temperature for 10 min. After the extraction, the liquid in the centrifuge tube was aspirated and the obtained extraction material was subjected to subsequent RCA.

The non-enriched (original) sample solution was amplified as a control. The volume of the RCA reaction was 20 μL, containing 10 μL of RCA mastermix, 2 μL of sample solution, 2 μL of circular probe (sequence: CACGC-GATCCGCAACTATACAACCTACTACCT-CAACACCCTCCAACCACCAAGGC AATGTA-CACGAATTCGCCGAACG), and 6 μL of water. The reaction system was mixed well and then incubated at 65° C. for isothermal amplification. The reaction duration was 1.5 h, which was called original solution amplification.

For solid phase extraction material, 10 μL of RCA master mix, 2 μL of circular probe and 8 μL of water were added to the centrifuge tube containing the material. The reaction system was mixed well and then incubated at 65° C. for isothermal amplification. The reaction duration was 1.5 h, which was called in situ amplification.

Figure 2:
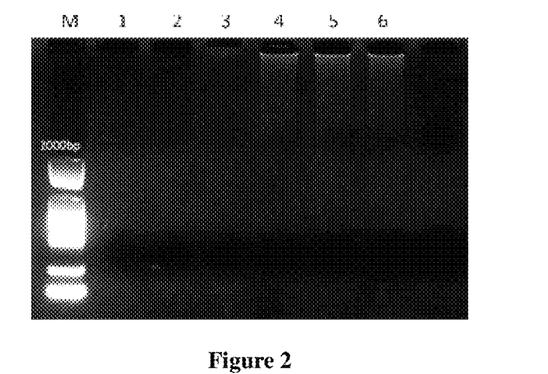
FIG. 2 shows the enrichment of miRNA (let-7a) by rGO modified magnetic beads; M is a DNA marker, lanes 1-3 are original solution amplifications, lanes 4-6 are in situ amplifications.

The products of original solution amplification and in situ amplification were subjected to electrophoresis, respectively. The results were shown in FIG. 2: M was a DNA marker, lanes 1-3 were original solution amplification, and lanes 5-8 were in situ amplification. As shown in FIG. 2, in the sample solution before the enrichment, the concentration of let-7a was not sufficient to be amplified to generate enough RCA products to show a bright band in gel electrophoresis. However, after the enrichment by rGO modified magnetic beads, the amount of RCA products was significantly increased, and bright bands can be seen in the electrophoresis picture. This experiment demonstrates that rGO modified magnetic beads are capable of efficiently enriching miRNA and undergoing in situ amplification.

3. Ability to Distinguish SNP by Amino Magnetic Beads and rGO Modified Magnetic Beads Amino magnetic beads mainly rely on electrostatic adsorption to capture nucleic acids, while graphene solid phase extraction materials mainly use π-π interaction to capture single-stranded nucleic acids. For the capture of miRNAs, they have similar effects and graphene-modified solid phase extraction materials show no advantage. However, the following experiment demonstrates that the rGO modified magnetic beads can efficiently distinguish homologous miRNAs but not the amino acid beads.

The miRNAs used in this example were let-7a and let-7d, which have a difference of two bases. The ring probe used in this example was probe designed for let-7a.

First, 25 µL each of let-7a and let-7d sample solutions (final concentration of 10 nM) were prepared. 0.5 µL of the rGO modified magnetic beads prepared in Example 3 (extraction material) was weighed in a 0.2 mL centrifuge tube. 20 µL each of the sample solutions was added to the centrifuge tube containing the extraction material, and the extraction material and the solution were mixed well by vortex or reverse mixing. Extraction was carried out at room temperature for 10 min. After the extraction, the liquid in the centrifuge tube was aspirated and the obtained extraction material was subjected to subsequent RCA. The non-enriched (original) sample solution was amplified as a control; sample enriched by unmodified amino magnetic beads was also set as control for RCA.

10 µL of RCA mastermix, 2 µL of circular probe (sequence: CACGCGATCCGCAACTATACAACCTAC-TACCTCAACACCCTCCAACCACCAAGGC AATGTA-CACGAATTCGCCGAACG), and 8 µL of water were added to each centrifuge tube containing the extraction materials after extraction. The reaction system was mixed well and then incubated at 65° C. for isothermal amplification. The reaction duration was 1.5 h. The amplification products were subjected to electrophoresis, respectively. The results were shown in FIG. 3.

Figure 3:
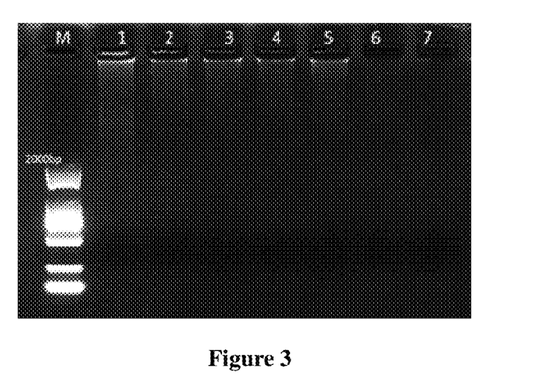
FIG. 3 shows the identification of homogeneous miRNAs by rGO modified beads in the examples. Lanes 1 and 2 are amplifications for let-7a and let-7d by normal RCAs; lanes 3 and 4 are in situ RCA of let-7a and let-7d after extracting by amino beads; lanes 5 and 6 are in situ RCA of let-7a and let-7d after extracting by rGO modified magnetic beads; 7 is a negative control experiment.

As shown in FIG. 3. Lane 1 and Lane 2 were amplifications of let-7a and let-7d by normal RCA with a reaction volume of 20 µL.

The amplification system of Lane 1 contained 10 µL of mastermix, 2 µL of let-7a (total amount of 200 nmol), 2 µL of circular probe and 6 µL of water.

The amplification system of lane 2 contained 10 µL of RCA mastermix, 2 µL of let-7d (total amount 200 nmol), 2 µL of circular probe and 6 µL of water.

Lanes 3 and 4 were in situ amplifications of the let-7a and let-7d (total amount 200 nmol, respectively) from amino magnetic beads without rGO modification.

Lane 5 and Lane 6 were in situ amplifications of let-7a and let-7d (total amount 200 nmol, respectively) from rGO modified magnetic beads.

Lane 7 was the negative control experiment.

There were bands shown in lanes 2 and 4, indicating that normal RCA and amino magnetic beads cannot distinguish between homologous miRNAs; while lane 6 has no obvious band, indicating that rGO modified magnetic beads have the ability of distinguishing homologous miRNAs.

4. Comparison of Adsorption Capacity of rGO Modified Magnetic Beads for Different Types of Nucleic Acid The present invention has for the first time found and confirmed that rGO modified materials can effectively adsorb miRNAs but not genomic DNA (gDNA) and mRNA, and thus can be used to extract miRNAs from complex nucleic acid solutions. While the most common commercially available silicon-based materials are not capable of differentially adsorbing miRNAs, gDNA, or mRNA.

In the experiments, the extraction volume was fixed at 20 µL, containing 20 nM Tris-HCl (pH=8.0), 5 mM $MgCl_2$, 100 nM NaCl, and 15 ng of nucleic acid (miRNA, gDNA, and mRNA, respectively), water as balance. 20 µL sample was extracted with rGO modified magnetic beads for 10 min. PCR was performed to verify the changes in nucleic acid content in the pre-extracted sample and in the supernatant after extraction.

Figure 4:
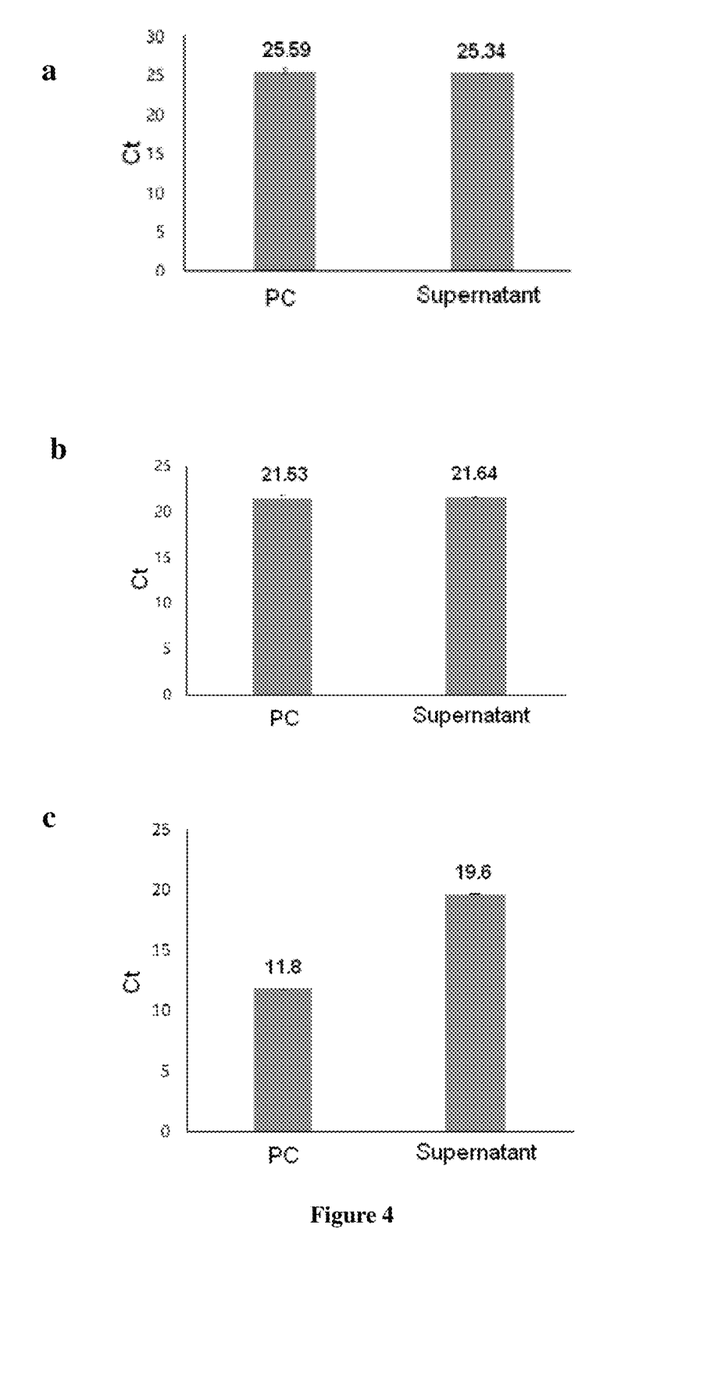
FIG. 4 shows the selective adsorption of rGO modified beads for miRNA, gDNA, and mRNA. PC is the test of the nucleic acid amount in the original sample; supernatant is the test of the nucleic acid amount in the supernatant after adsorption, and the ordinate is the Ct value of the PCR; (A) shows the gDNA adsorption; (B) shows the mRNA adsorption; (C) shows the miRNA adsorption.

The nucleic acid used in FIG. 4(A) was a human gDNA and the target of amplification was the β-actin gene. It can be seen from the Ct value of PCR that there is no change in the nucleic acid content of the samples before and after extraction, indicating that the material has no adsorption effect on gDNA.

The nucleic acid used in FIG. 4(B) was a total RNA. The change of GAPDH mRNA content was determined by RT-qPCR. It can be seen from the Ct value of PCR that there is no change in the nucleic acid content of the samples before and after extraction, indicating that the material has no adsorption effect on mRNA.

The sample used in FIG. 4(C) was let-7a miRNA. The change of content before and after extraction was determined by RT-qPCR. It can be seen that the difference in Ct values before and after extraction was 7.8. If the amplification efficiency was 2, then 99.55% of let-7a miRNA was adsorbed.

In FIG. 4(A) to (C), Ct values of the negative controls were 38.87, N/A (not detected) and 32.47, respectively.

The above experiments show that the rGO modified magnetic beads can effectively adsorb miRNA but not gDNA and mRNA.

5. Enrichment of miRNA Sample by rGO modified magnetic beads

In situ RCA was performed on the low concentration nuclei acid solutions without enrichment. The RCA system was 20 µL, containing 10 µl of RCA mastermix, 2 µl of miRNA sample (let-7a), 2 µL of circular probe (sequence: CACGCGATCCGCAACTATACAACCTACTACCT-CAACACCCTCCAACCACCAAGGC AATGTA-CACGAATTCGCCGAACG) and 6 µL of water.

100 µL, of miRNA sample was extracted by rGO modified magnetic solid phase extraction material. After the extraction, the rGO modified magnetic solid phase extraction material was subjected to in situ RCA. The reaction system was 20 µL, containing 10 µL of mastermix, rGO modified magnetic beads, 2 µL of circular probe (sequence: CACGC-GATCCGCAACTATACAACCTACTACCT-CAACACCCTCCAACCACCAAGGC AATGTA-CACGAATTCGCCGAACG) and 8 µl of water.

Figure 5:
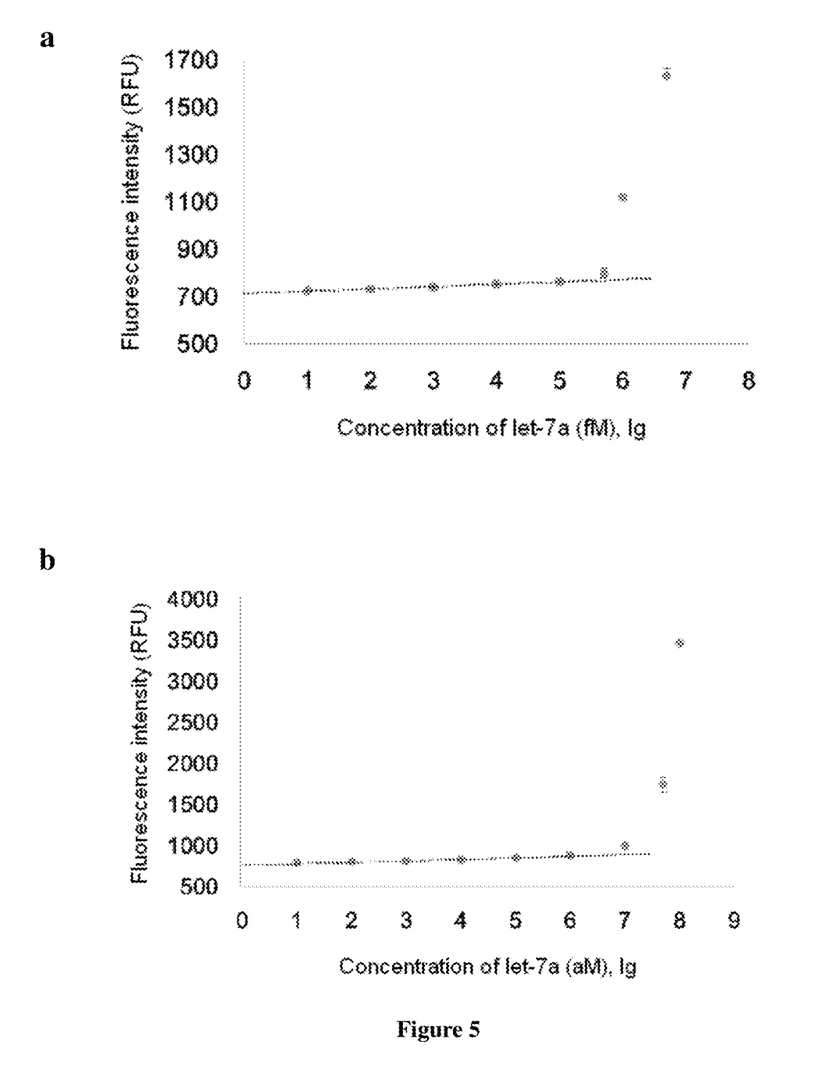
FIG. 5 shows the enrichment of miRNA by rGO modified magnetic beads; (A) shows that without enrichment, RCA detection limit for a miRNA sample is 1.318 pM (3σ); (B) shows that RCA detection limit for a miRNA sample is 53.4 fM (3σ) after enrichment by a modified magnetic beads.

As shown in FIG. 5(A), without enrichment, the detection limit of RCA for miRNA sample was 1.318 pM (3σ), while after the enrichment by magnetic material, the detection limit of RCA for miRNA sample reached 53.4 fM (3σ) (FIG. 5(B)), reducing by about 25 times. It can be concluded that the magnetic material can be used for the detection of low concentration miRNA samples.

The above are merely preferred embodiments of the present invention, and it should be pointed out that those of ordinary skill in the art can also make several improvements and improvements without departing from the principle of the present invention. These improvements and modifications should also be regarded as the scope of protection of the present invention.

What is claimed is:

1. A method of enriching nucleic acid, comprising:
   mixing a sample with a solid phase extraction material; and
   separating the solid phase extraction material;
   wherein the solid phase extraction material is glass beads or magnetic beads modified with reduced graphene oxide, and the nucleic acid is miRNA.

2. The method according to claim 1, wherein the diameter of the glass beads is 100 μm to 300 μm.

3. The method according to claim 1, wherein the reduced graphene oxide has a lateral size of 0.5 μm to 2 μm.

4. The method according to claim 1, wherein the method further comprises:
   washing the solid phase extraction material; and
   eluting the nucleic acid.

5. A method of detecting miRNA, comprising
   mixing a nucleic acid sample enriched by the method according to claim 1 with a probe; and
   amplifying and detecting an amplification product by electrophoresis.

6. The method according to claim 5, wherein the amplification is rolling circle amplification (RCA).

7. The method according to claim 1, wherein the diameter of the magnetic beads is 10 nm to 5 μm.

* * * * *

SEQUENCE LISTING

```
Sequence total quantity: 3
SEQ ID NO: 1           moltype = DNA  length = 22
FEATURE                Location/Qualifiers
misc_feature           1..22
                       note = ssDNA
source                 1..22
                       mol_type = other DNA
                       organism = synthetic construct
SEQUENCE: 1
tgaggtagta ggttgtatag tt                                              22

SEQ ID NO: 2           moltype = RNA  length = 22
FEATURE                Location/Qualifiers
misc_feature           1..22
                       note = miRNA let-7a
source                 1..22
                       mol_type = other RNA
                       organism = synthetic construct
SEQUENCE: 2
tgaggtagta ggttgtatag tt                                              22

SEQ ID NO: 3           moltype = DNA  length = 78
FEATURE                Location/Qualifiers
misc_feature           1..78
                       note = Circular Probe
source                 1..78
                       mol_type = other DNA
                       organism = synthetic construct
SEQUENCE: 3
cacgcgatcc gcaactatac aacctactac ctcaacaccc tccaaccacc aaggcaatgt     60
acacgaattc gccgaacg                                                   78
```